United States Patent [19]
Silvestri

[11] Patent Number: 5,569,842
[45] Date of Patent: Oct. 29, 1996

[54] AUTOMATED SYSTEM FOR IDENTIFYING AND ANALYZING DIFFERENT TYPES OF USED LUBRICANTS

[75] Inventor: Regan L. Silvestri, Orange Village, Ohio

[73] Assignee: Man-Gill Chemical Company, Cleveland, Ohio

[21] Appl. No.: 412,079

[22] Filed: Mar. 28, 1995

[51] Int. Cl.$^6$ .............................. G01N 7/00; G01N 1/10; B01D 17/02
[52] U.S. Cl. .......................... 73/53.05; 73/61.48; 436/60; 356/303; 356/326
[58] Field of Search ............................... 73/53.05, 61.48; 436/60; 356/303, 319, 326

[56] References Cited

U.S. PATENT DOCUMENTS

| | | | |
|---|---|---|---|
| 3,024,642 | 3/1962 | Jones, Jr. | 73/54 |
| 4,289,020 | 9/1981 | Paap | 250/43.5 |
| 5,420,041 | 5/1995 | Matsushita et al. | 436/61 |
| 5,457,528 | 10/1995 | Tobias | 356/300 |

FOREIGN PATENT DOCUMENTS 2246082  1/1992  United Kingdom ................... 73/61.48

OTHER PUBLICATIONS

Instrumental Methods Of Analysis Fifth Edition, Hobart H. Willard et al., "Infrared Spectroscopy", D. Van Nostrand Company, p. 150, Chapter 6.

Bio–Rad Digilab Division, "Automated Used Oil Analysis System", Literature.

Annual Book of ASTM Standards, vol. 10.03, D2144–90, American Society For Testing And Materials, 1993, "Standard Test Methods for Examination of Electrical Insulating Oils by Infrared Absorption", pp. 257–260.

CRC Handbook of Lubrication, vol. 1, E. Richard Booser, CRC Press, Inc., Boca Raton, FL, 1983, p. 86.

Galactic Software Brochure, Galactic Add–On Applications.

*Primary Examiner*—Hezron E. Williams
*Assistant Examiner*—J. David Wiggins
*Attorney, Agent, or Firm*—Renner, Otto, Boisselle & Sklar, P.L.L.

[57] ABSTRACT

An apparatus for automatically identifying and analyzing different types of used lubricants is provided. The apparatus includes a spectrometer for obtaining electromagnetic absorption spectrum data for a lubricant, a computer for processing the spectrum data to determine at least one characteristic chemical property of the lubricant, for identifying a lubricant type based on the at least one characteristic chemical property, and for analyzing the electromagnetic absorption spectrum data as a function of the lubricant type to evaluate a use characteristic of the lubricant, and a display for outputting information relating to the use characteristic of the lubricant.

25 Claims, 6 Drawing Sheets

AUTOMATED SYSTEM FOR IDENTIFYING AND ANALYZING DIFFERENT TYPES OF USED LUBRICANTS

TECHNICAL FIELD

The present invention relates generally, as is indicated, to an automated system for identifying and analyzing different types of used lubricants. More specifically, the present invention relates to an system capable of discriminating between different types of mineral and synthetic lubricants and automatically evaluating one or more use characteristics of the lubricants based on the type thereof.

BACKGROUND OF THE INVENTION

Infrared spectroscopy and the study of used lubricating oils is known in the art. Infrared spectroscopy involves the twisting, bending, rotating and vibrational motions of atoms in a molecule. Upon interaction with infrared radiation, portions of the incident radiation are absorbed at particular wavelengths. The multiplicity of vibrations occurring simultaneously produces a highly complex absorption spectrum characteristic of the molecules. See, e.g., Willard et al., Instrumental Methods of Analysis, 5th ed., Chap. 6, D. Van Nostrand Company (1974). In the past, infrared spectroscopy has been used to analyze lubricants for purposes of determining lubricant degradation, contamination, additive depletion and other use parameters or characteristics. Typically, a system operator would insert a sample of lubricant into a spectrometer which would provide a spectrum of the sample. A computer coupled to the spectrometer would process the spectrum data in order to determine one or more of the above parameters.

Unfortunately, these conventional systems suffered from various drawbacks. For example, each system was designed to analyze only a particular type of lubricant. Thus, it was necessary to know the type of lubricant which was to be analyzed prior to having the system perform the actual analysis. In the event a system designed to analyze one type of lubricant was accidentally used to analyze a different type of lubricant, the system could produce erroneous results. If a system designed to evaluate mineral lubricant was used to evaluate a synthetic lubricant, the system could produce output information which did not accurately analyze the use characteristics of the lubricant. This meant that a system operator had to be careful to ensure that a system designed to analyze a particular type of lubricant was not used to analyze an incompatible lubricant. It also meant that if the system operator did not know the type of lubricant to be analyzed, the system operator had to first find out such information before knowing whether a given system could provide an accurate analysis. This could result in delays and imposed additional responsibilities on the system operator, thereby increasing the costs associated with system operation.

Furthermore, because each system was limited in application to a particular type of lubricant, different and/or reconfigured systems were required for analyzing different types of lubricants. This could lead to higher system costs as a result of having to obtain and operate two or more systems each dedicated to a respective type of lubricant.

In view of the aforementioned shortcomings associated with conventional systems for analyzing lubricants, there is a strong need in the art for a system which does not require prior knowledge of the type of lubricant being evaluated in order to ensure accurate results. More particularly, there is a strong need in the art for a system which can identify automatically the type of lubricant being analyzed and can automatically analyze the lubricant based on the identified type. There is a strong need in the art for a system which does not require the system operator to know the particular type of lubricant, thereby reducing the potential for error in the analysis and reducing operating costs. In addition, there is a strong need for a system which is capable of detecting and analyzing several different types of lubricants automatically so as to obviate the need for several separate and/or reconfigured systems.

The present invention addresses each of the above-mentioned shortcomings found in conventional systems as will be appreciated based on the following description.

SUMMARY OF THE INVENTION

In accordance with one aspect of the present invention, an apparatus is provided for automatically identifying a type of lubricant. The apparatus includes means for obtaining electromagnetic absorption spectrum data for a lubricant; automated means for processing the spectrum data to determine at least one characteristic chemical property of the lubricant and for identifying a lubricant type based on the at least one characteristic chemical property; and means for outputting the, lubricant type.

According to another aspect of the present invention., an apparatus for automatically identifying and analyzing different types of used lubricants is provided. The apparatus includes means for obtaining spectrum data for a lubricant; automated means for processing the electromagnetic absorption spectrum data to locate at least one characteristic chemical property of the lubricant, for identifying a lubricant type based on the at least one characteristic chemical property, and for analyzing the electromagnetic absorption spectrum data as a function of the lubricant type to evaluate a use characteristic of the lubricant; and means for outputting information relating to the use characteristic of the lubricant.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DESCRIPTION OF THE PREFERRED EMBODIMENT

The present invention will now be described with reference to the drawings, wherein like reference numerals are used to refer to like elements throughout.

Figure 1:
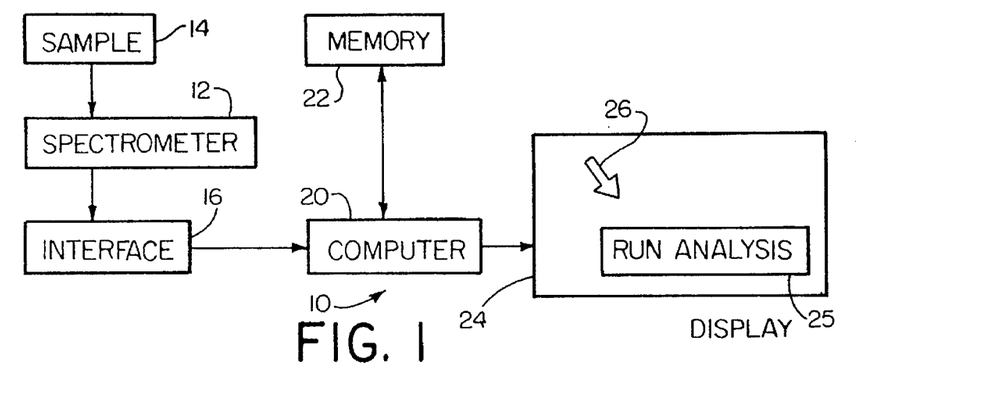
FIG. 1 is a block diagram of an automated system for identifying and analyzing different types of used lubricants in accordance with the present invention.

Referring initially to FIG. 1, an automated system for identifying and analyzing different types of used lubricants is generally designated 10. The system 10 includes a spectrometer 12 for obtaining spectrum data of a lubricant sample 14. The lubricant sample 14 can be virtually any lubricant such as used mineral oil, organic ester or phosphate ester lubricants as referred to specifically herein, as well as other types such as perfluoropolyethers, silicones, glycols, blends of poly-alpha-olefins (PAOs) with organic esters, etc. A system operator inserts the sample 14 into the spectrometer 12 which obtains the spectrum data according to conventional techniques. In the exemplary embodiment, the spectrometer 12 is a Fourier transform infrared (FT-IR) spectrometer such as a Model FTS 155 or Model FTS 165 spectrometer available from Bio-Rad Laboratories, Cambridge, Mass., U.S.A. Such spectrometers provide infrared absorbance spectrum data for the sample 14 as is conventional.

The spectrometer 12 outputs the spectrum data via an interface 16 to a computer 20 which stores the spectrum data in memory 22 for processing and analysis. The interface 16 can be any interface which allows the spectrum data provided from the spectrometer to be received and stored by the computer 20. For example, in the event the spectrometer 12 were to provide the spectrum data as an analog output in the form of absorbance vs. wavenumber, the interface 16 could include an analog-to-digital converter to convert the analog output to digital data which can be stored and analyzed by the computer 20. Also, it will be appreciated that although FIG. 1 shows the interface 16 and memory 22 as being separate from the computer 20, the interface and memory can be part of the computer 20 itself. For example, the computer 20 can be a general purpose computer such as an IBM-compatible personal computer, with the interface 16 representing an interface card within the computer 20 and the memory 22 representing a hard disk or the like.

The system 10 also includes a display 24 and/or printer (not shown) connected to the computer 20. The display 24 or printer serves as an interface between the system operator and the system 10. The system operator instructs the system 10 to determine the type of lubricant and run an analysis by "clicking" on icon 25 on the display 24 with a pointer 26, for example. According to the exemplary embodiment of the present invention and as described more fully below, the computer 20 is programmed to analyze the spectrum data provided by the spectrometer 12 in order to identify automatically the type of lubricant which is represented by the sample 14. In addition, the computer 20 is programmed to analyze the spectrum data for one or more use characteristics based on the type of lubricant represented by the sample 14. As referred to herein, a "use characteristic" relates to a property of the lubricant sample 14 which is indicative of the condition of the lubricant. For example, lubricant degradation (e.g., oxidation, nitration, sulfates) lubricant contamination (e.g., water, soot, Freon, glycol, fuel), and additive depletion (e.g., antioxidant and antiwear levels) in the lubricant sample are known use characteristics or indicators for evaluating the integrity of used lubricants.

For the reasons described more fully below, the system 10 is able to identify automatically the type of lubricant and, as a result, does not require that the system operator make sure that only a compatible type of lubricant is analyzed in the system as in the past. Moreover, the system 10 automatically identifies the type of lubricant and thereafter is able to perform an appropriate analysis based on the type of lubricant. Thus, the same system 10 can be used to analyze different types of lubricants without risk that the system will perform the wrong analysis in the event of an incompatible lubricant. The system outputs on the display 24 and/or stores to memory, prints, etc. the type of lubricant which is represented by the sample 14 and the relevant use characteristics associated with the sample 14 based on the type of lubricant.

Figure 2:
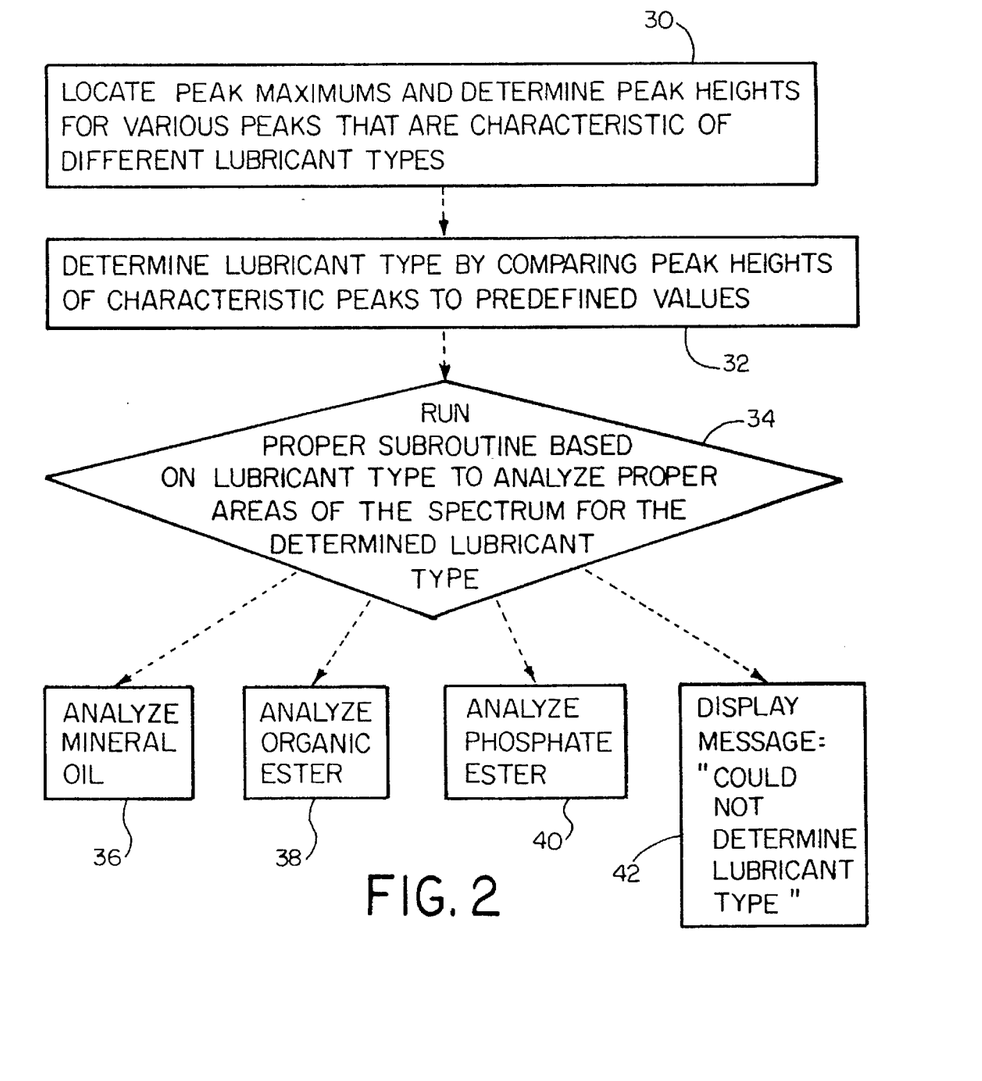
FIG. 2 is a flowchart representing the operation of the system of FIG. 1 in accordance with the present invention.
Figure 6:
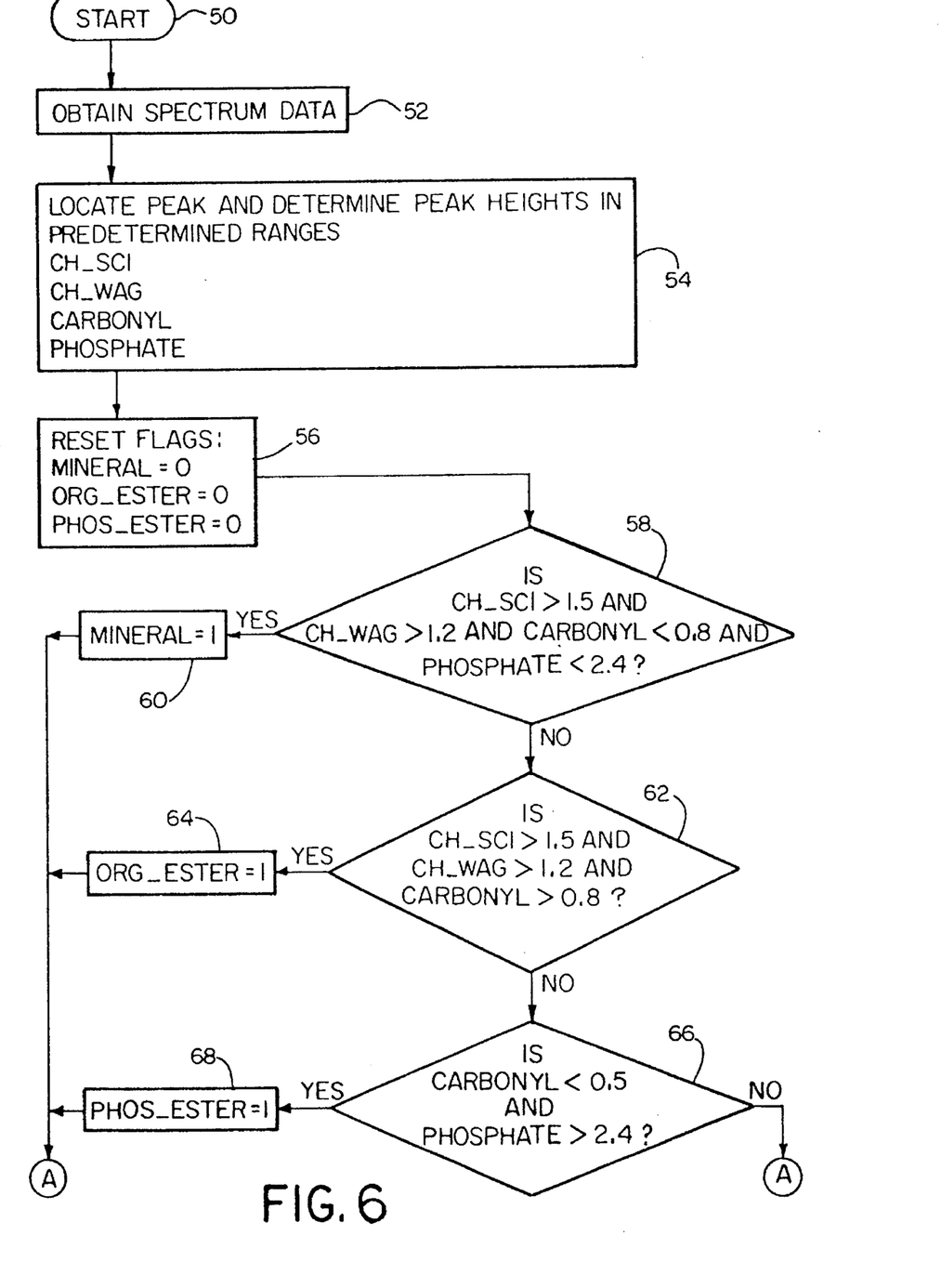
FIGS. 6 and 7 provide a detailed flowchart representing in more detail the system operation shown in FIG. 2 in accordance with the present invention.
Figure 7:
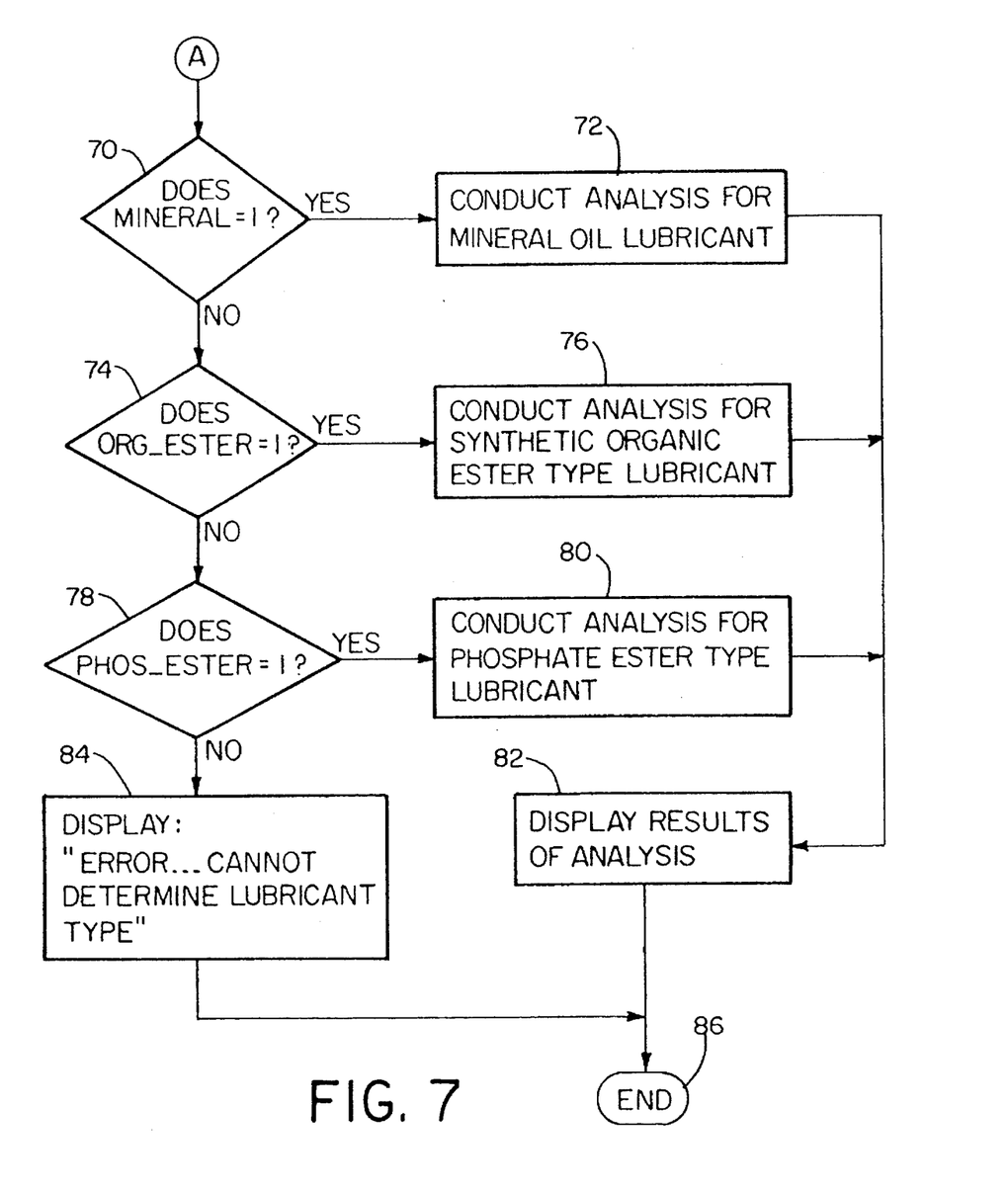

FIGS. 2, 6 and 7, as are discussed below, illustrate the operation of the system 10. It will be appreciated that a person having ordinary skill in the field of computer programming would be able to program the computer 20 to carry out the respective functions shown in relation to FIGS. 2, 6 and 7 based on the disclosure provided herein. As a result, further detail is omitted for sake of brevity.

Referring now to FIG. 2, the general operation of the system 10 will be explained. Beginning with step 30, the spectrometer 12 obtains the spectrum data from the sample 14 and provides such data to the computer 20. Such data is typically in the format of absorbance value vs. wavenumber, although other data formats are also possible as will be appreciated. Based on a predefined criteria as discussed in more detail below in connection with FIGS. 3–7, the computer 20 analyzes the spectrum data to locate peak maximums to determine peak heights in the spectrum data for various peaks that are characteristic of different types of lubricant. In step 32, the computer 20 compares the peak heights found in step 30 to predefined values representative of different lubricant types. As is explained more fully below in connection with FIGS. 3–5, different types of lubricants have been found to have different characteristic peaks in their respective spectra. By comparing the peak values found in the spectrum data for the sample 14 with the predefined peak values characteristic of different types of lubricants, the computer 20 identifies the lubricant type for the sample 14.

According to the exemplary embodiment, the computer 20 determines in step 32 whether the sample 14 is a mineral oil, an organic ester, a phosphate ester, or some other type of lubricant. It will be appreciated herein that the classification of mineral oil can also include poly-alpha-olefins (PAOs) since both are hydrocarbons and both exhibit the same degredation mechanism. In step 34, the computer 20 runs an appropriate subroutine for analyzing one or more use characteristics of the sample based on the lubricant type of the sample. Generally, the computer 20 looks to different ranges in the sample spectrum data to assess the use characteristics of the sample. The particular ranges in the sample spectrum data to be evaluated are dependent upon the type of lubricant. Because the computer 20 automatically determines the type of lubricant the sample represents, it is certain that the computer 20 will analyze the appropriate ranges in the sample spectrum data in order to evaluate the use characteristics. The above-discussed conventional systems which did not always know the type of lubricant could ultimately analyze the wrong ranges in the sample spectrum data when analyzing the used lubricants. As a result, such conventional systems could produce erroneous results.

Thus, in step 34 the computer 20 branches to the appropriate subroutine for analyzing the used lubricant based on the lubricant type. For example, if the system determines that the sample 14 is a mineral oil in step 32, the system proceeds to step 36 for analyzing a mineral oil according to a predefined criteria. Similarly, if the system determines that the sample is an organic ester or phosphate ester in step 32, the system proceeds to steps 38 and 40, respectively. In the event the system 10 does not recognize the sample 14 as being either a mineral oil, organic ester or phosphate ester in step 32, the system proceeds to step 42 in which the computer displays a message on the display 24 indicating that the lubricant type cannot be determined. As a result, the system operator will be alerted to the fact that further analysis of the lubricant is not available, thereby avoiding the possibility of erroneous results.

Figure 3:
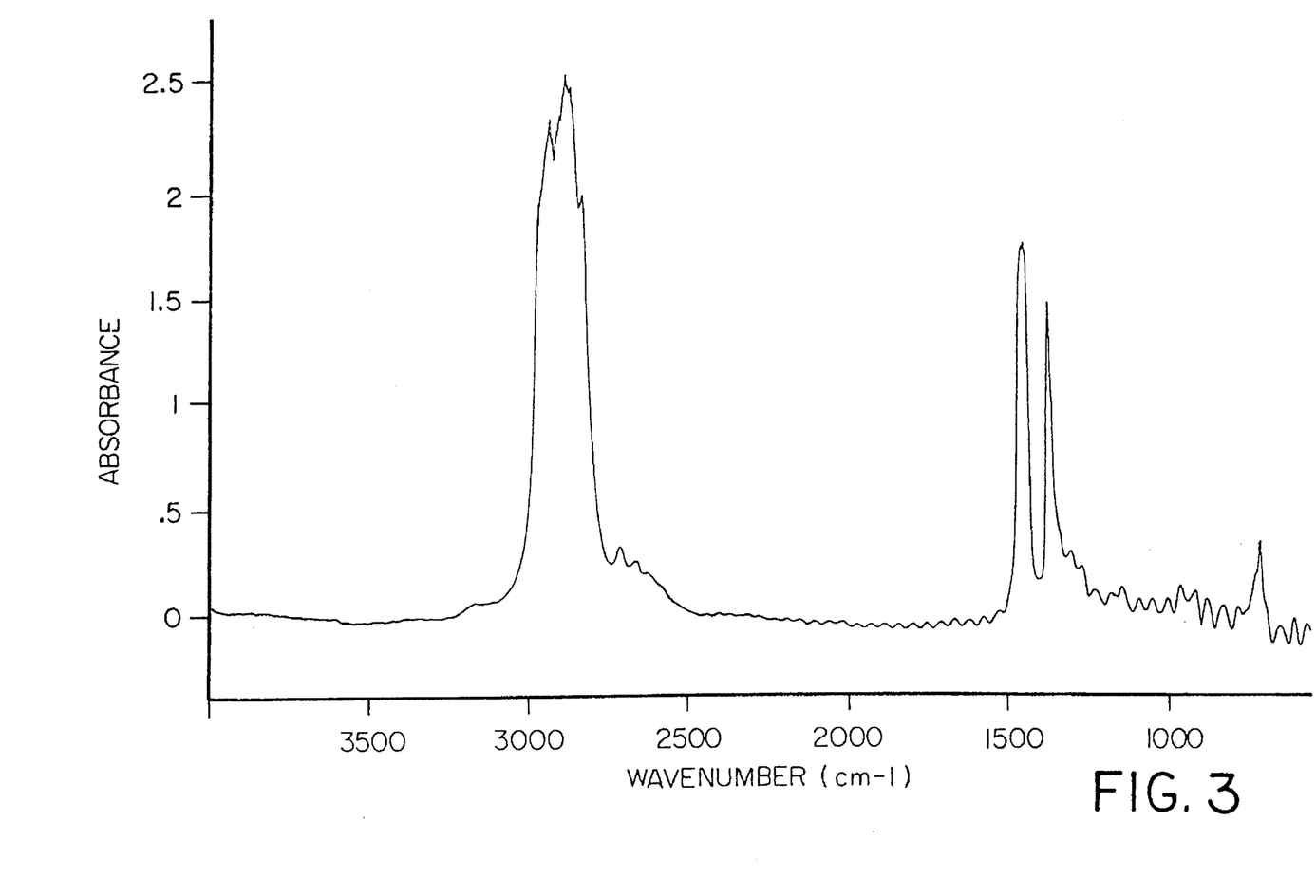
FIGS. 3 thru 5 are graphs representing exemplary spectrum data for mineral oil, organic ester and phosphate ester lubricants, respectively.
Figure 4:
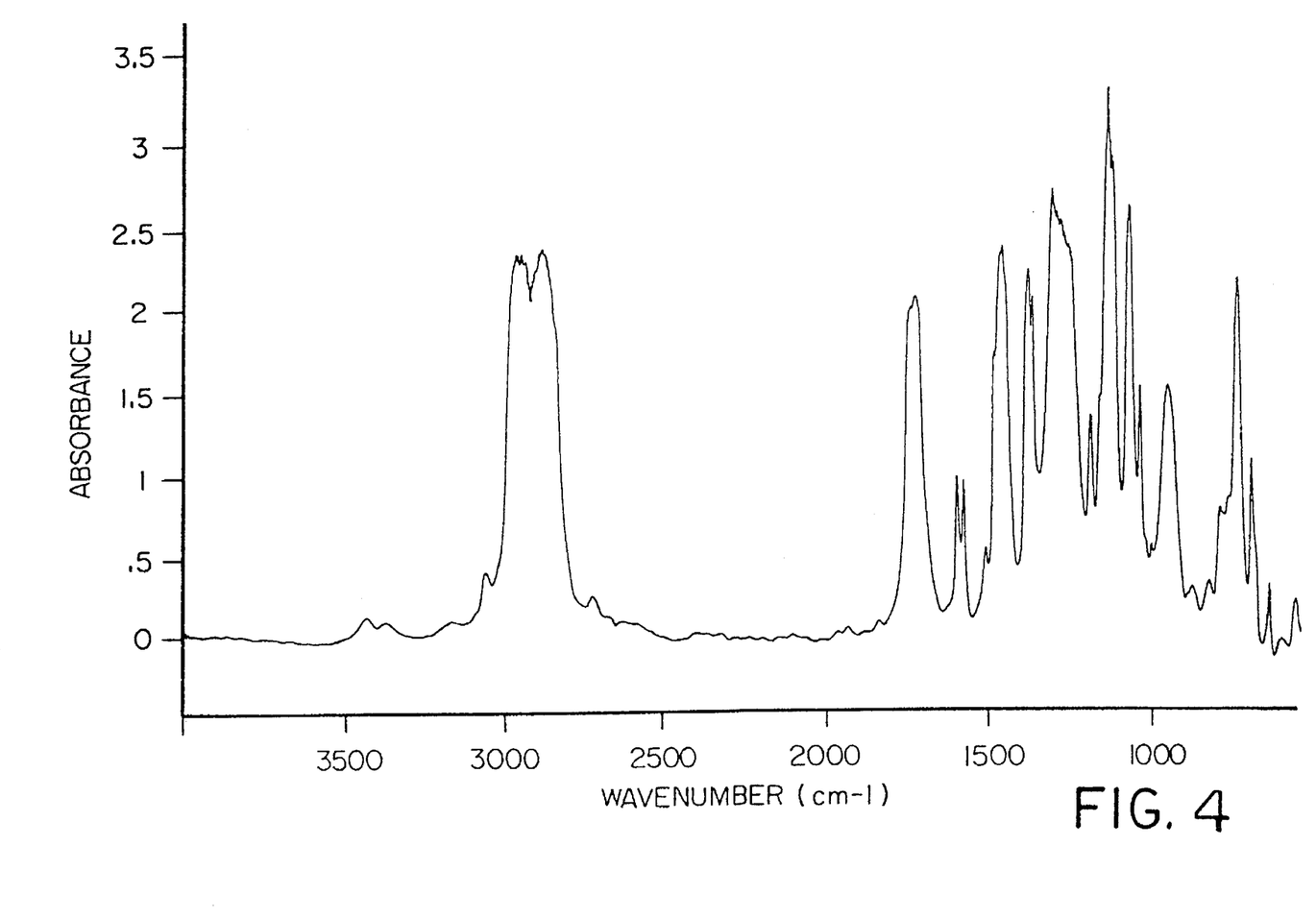
Figure 5:
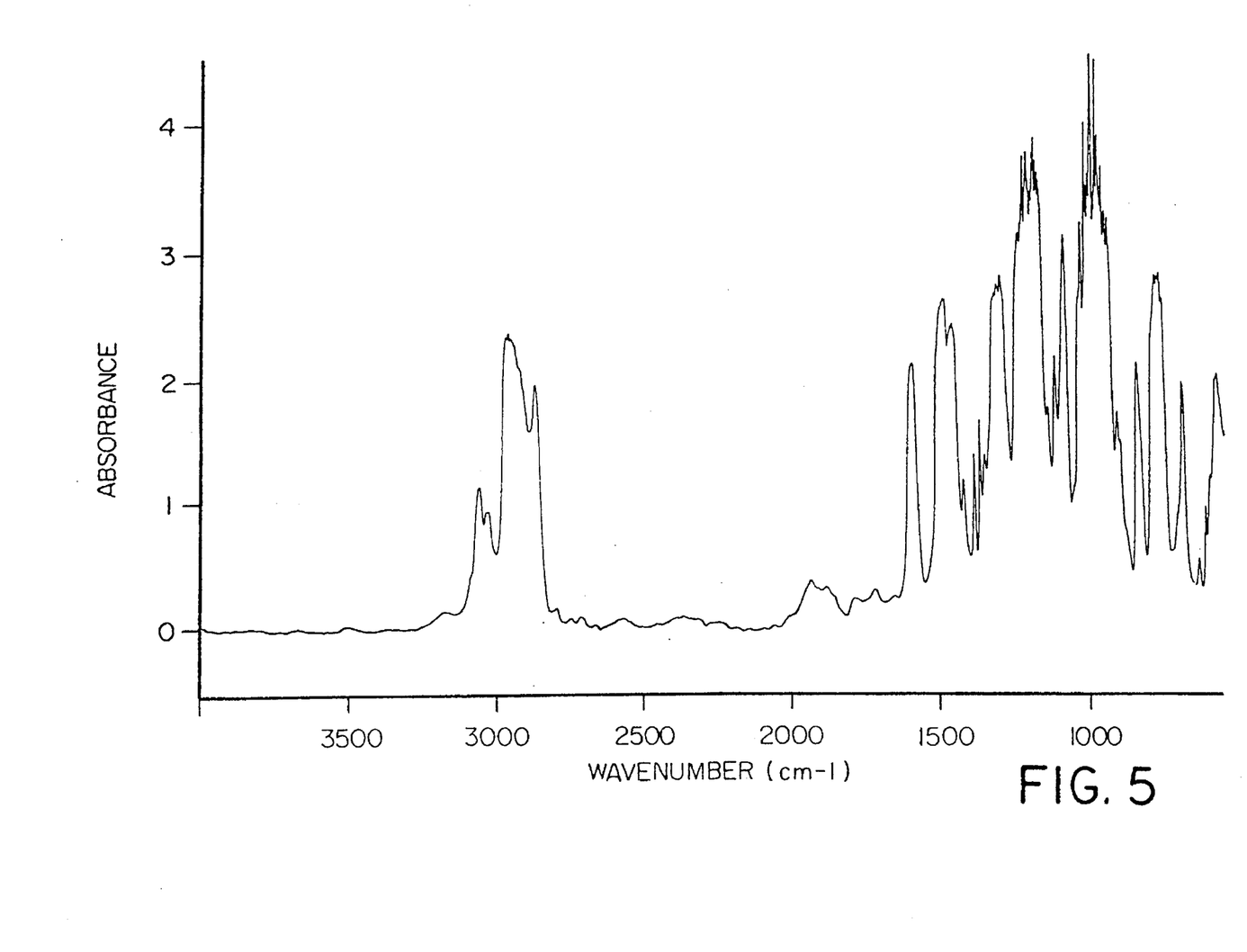

FIGS. 3–5 exemplify typical spectrum data for mineral oil, organic ester, and phosphate ester lubricants, respectively. The spectrum data in FIGS. 3–5 is shown graphically whereby the vertical axis represents the absorbance level and the horizontal axis represents the wavenumber in $cm^{-1}$. As can be seen in FIG. 3, the mineral oil spectrum includes a relatively large $CH_2$ scissoring component in the range $1468\ cm^{-1}$ to $1448\ cm^{-1}$, and a relatively large $CH_2$ wagging component in the range $1380\ cm^{-1}$ to $1374\ cm^{-1}$. At the same time, the mineral oil spectrum has a relatively small carbonyl component in the range $1800\ cm^{-1}$ to $1700\ cm^{-1}$. FIG. 4 illustrates how a typical organic ester spectrum also has relatively large $CH_2$ scissoring and wagging components in the ranges $1468\ cm^{-1}$ to $1448\ cm^{-1}$, and $1380\ cm^{-1}$ to $1374\ cm^{-1}$, respectively. However, the organic ester spectrum also includes a sizable carbonyl component in the range $1800\ cm^{-1}$ to $1700\ cm^1$. The spectrum for phosphate esters, on the other hand, has very little in the way of a carbonyl component while at the same time having a relatively large phosphate component in the range $1250\ cm^{-1}$ to $1120\ cm^{-1}$.

Based on such knowledge of the relationships between the spectra for the different types of lubricants, the computer 20 is programmed to analyze the sample spectrum data in order to determine the type of lubricant. More specifically, the computer 20 compares the sample spectrum data to predefined thresholds which are established based on the spectrum relationships between the different types of lubricants. For example, FIGS. 6 and 7 illustrate in detail how the system 10 identifies and analyzes the lubricant sample according to the preferred embodiment. In step 50, the system 10 begins the analysis. The system enters step 50 upon the system operator placing the sample in the spectrometer 12 and "clicking" on the icon 25 on the display 24 (FIG. 1). Alternatively, a keyboard command or the like is used to initiate the analysis as will be appreciated.

The system 10 proceeds from step 50 to step 52 in which the spectrometer 12 obtains the spectrum data for the sample and provides the data to the computer 20 where it is stored in memory 22 for processing. Next, in step 54 the computer 20 analyzes the spectrum data obtained from the sample 14 to determine the peak absorbance values "ch_sci", "ch_wag", "carbonyl", and "phosphate" in corresponding predefined ranges as follows:

(a) "ch_sci" (representing the $CH_2$ scissoring component) is equal to the maximum absorbance value in the range $1468\ cm^{-1}$ to $1448\ cm^{-1}$;

(b) "ch_wag" (representing the $CH_2$ wagging component) is equal to the maximum absorbance value in the range $1380\ cm^{-1}$ to $1374\ cm^{-1}$;

(c) "carbonyl" (representing the carbonyl component) is equal to the maximum absorbance value in the range $1800\ cm^{-1}$ to $1700\ cm^{-1}$; and (d) "phosphate" (representing the phosphate component) is equal to the maximum absorbance value in the range $1250\ cm^{-1}$ to $1120\ cm^{-1}$.

Next, in step 56 the computer 20 resets each flag "mineral", "org_ester" and "phos_ester" to zero. As will be appreciated, such flags can be maintained in the computer memory 22. Beginning in step 58, the computer 20 compares the peak absorbance values to predefined threshold values and determines whether the following conditions are satisfied:

i) ch_sci>1.5 AND
  ii) ch_wag>1.2 AND
  iii) carbonyl<0.8 AND
  iv) phosphate<2.4.

The actual values of the predetermined thresholds, e.g., 1.5, 1.2, etc., are determined based on known typical spectrum data for the different types of lubricants as discussed above in connection with FIGS. 3–5. Conditions i–iv have been found to be characteristic of mineral oil. Thus, if each of conditions i–iv are satisfied, the system 10 determines that the sample lubricant is a mineral oil and proceeds to step 60 where the computer 20 sets the "mineral" flag to 1.

If the conditions in step 58 are not satisfied, the system proceeds to step 62 in which the computer determines whether the following conditions are satisfied:

v) ch_sci>1.5 AND
  vi) ch_wag>1.2 AND
  vii) carbonyl>0.8.

Conditions v–vii, in this case, have been found to be characteristic of a synthetic organic ester type lubricant. Provided conditions v–vii are satisfied in step 62, the system concludes that the sample lubricant is an organic ester type lubricant and sets the "org_ester" flag to 1 in step 64.

In the event the conditions of steps 58 and 62 are not satisfied, the system proceeds to step 66 where the computer 20 determines whether the following conditions, representative of a phosphate ester, are satisfied:

viii) carbonyl<0.5 AND
  ix) phosphate>2.4.

If both conditions viii and ix are satisfied in step 66, the system determines that the sample lubricant is a phosphate ester type lubricant and proceeds to step 68 where the "phosphate" flag is set to 1. If the conditions in step 66 are not satisfied, the system proceeds directly to step 70 as shown in FIG. 7. Following steps 60, 64 and 68, the system automatically proceeds to step 70 as shown.

Based on the above described analysis, it will be appreciated that the system 10 is able to identify automatically the lubricant type of the sample 14. Additional types of lubricants (e.g., perfluoropolyethers, silicones, glycols, blends of poly-alpha-olefins (PAOs) with organic esters, etc.) can be similarly identified by programming the computer 20 to compare characteristics of the sample lubricant with predefined characteristics of the other known lubricant types. Although the present invention is described herein as being capable of identifying three different types of lubricants, such a construction is intended merely to be exemplary. It will be appreciated that the system could be configured to identify more or less than three different lubricants without departing from the scope of the invention.

Referring again to step 70, the computer 20 determines whether the "mineral" flag has been set to 1 so as to identify the sample lubricant as a mineral oil. If so, the system proceeds to step 72 where the system 10 conducts a predefined analysis of the sample lubricant based on the knowledge that the lubricant is a mineral oil. The analysis of step 72 is explained in more detail below together with the analysis of the other types of lubricants. If the "mineral" flag is not equal to 1 in step 70, the system proceeds to step 74 where the computer determines whether the "org_ester"

flag has been set to 1 so as to indicate that the sample 14 is an organic ester type lubricant. If yes, the system proceeds to step 76 in which the system analyzes the sample according to a predefined analysis for an organic ester type lubricant.

In the event the "org_ester" flag has not been set to 1 in step 74, the system proceeds to step 78 in which the computer determines whether the "phos_ester" flag has been set to 1, thus indicating that the sample 14 has been identified as being a phosphate ester type lubricant. If yes, the system proceeds to step 80 in which the system conducts a predefined analysis for phosphate ester type lubricants. Following each of steps 72, 76 and 80, the system proceeds to step 82 in which the computer displays on the display 24 and/or stores to memory or prints the results of the analysis. For example, the computer displays the type of lubricant together with the results of the use analysis based on the use characteristics for the particular type of lubricant.

If, in step 78, the "phos_ester" flag has not been set to 1, the system proceeds to step 84. In step 84, the computer displays via the display 24 or saves to memory, prints, etc. an error message indicating that the system cannot determine the lubricant type. Following steps 82 and 84, the system proceeds to step 86 where the analysis is completed.

Referring back to step 72 and the analysis of a mineral oil type lubricant, the actual analysis which is conducted will depend on the type of use information which is desired. For example, the amount of Freon in the mineral oil type sample 14, particularly as measured in the ranges of 1170 $cm^{-1}$ to 1065 $cm^{-1}$ and 935 $cm^{-1}$ to 860 $cm^{-1}$ of the sample spectrum data, has been found to be a useful measure of the integrity of the used lubricant. Thus, in step 72 the system measures the Freon content of the sample by integrating the area of the peaks that occur in the spectrum data within the ranges of 1170 $cm^{-1}$ to 1065 $cm^{-1}$ and 935 $cm^{-1}$ to 860 $cm^{-1}$. This information is then displayed via the display 24 in step 82. Another useful criteria for evaluating the use characteristics of the mineral oil type sample 14 has been found to be the sulfate content as represented in the range of 1150 $cm^{-1}$ to 1050 $cm^{-1}$ in the spectrum data. Thus, in step 72 the system 10 is also programmed to integrate the area of the peaks that occur in the spectrum data in the range of 1150 $cm^{-1}$ to 1050 $cm^{-1}$ to provide an indication of sulfate content. Such result is similarly displayed as an output.

Regarding the analysis of organic ester type lubricants as carried out in step 76, again the Freon content can serve as a useful indication of the integrity of the lubricant sample. However, in the case of organic ester type lubricants, it has been found that the Freon content is best represented in the ranges of 910 $cm^{-1}$ to 855 $cm^{-1}$ and 840 $cm^{-1}$ to 768 $cm^{-1}$ of the sample spectrum data. As a result, the system 10 is programmed to integrate the peaks of the spectrum data in such ranges in step 76 to evaluate the Freon content in connection with organic ester type lubricants. It will be appreciated that due to peaks inherent in the spectrum of an unused organic ester, analysis of the Freon component using the same ranges as those used for analyzing mineral oils could result in a false Freon positive reading. The present invention is able to avoid such errors.

Similarly, the system in step 80 is programmed to carry out a predefined analysis of phosphate ester type lubricants based on the spectrum data. The particular analyses which the system 10 performs upon determining the lubricant type of the sample 14 can be any of a variety of analyses. Such analyses can also be based on the integration of particular ranges in the spectrum data of the sample and relate to Freon or sulfate content as noted above, or other parameters such as water contamination, antioxidant values and antiwear agent values in the lubricant sample as previously mentioned, for example. The system 10 is particularly useful in that to the extent any of the analyses differ based on the type of lubricant (as in the particular Freon bands discussed above), the system automatically determines the type of lubricant and carries out the appropriate analysis.

Although the invention has been shown and described with respect to certain preferred embodiments, it is obvious that equivalents and modifications will occur to others skilled in the art upon the reading and understanding of the specification. For example, although the exemplary embodiment determines the type of lubricant based on an analysis of the peak heights in the spectrum data, it will be appreciated that other techniques could be used. In another embodiment, for example, the computer memory 22 has stored therein complete spectrum data for different types of lubricants. Instead of comparing peak values, the computer 20 is programmed to compare the complete spectrum data for the sample 14 with the various spectrum data stored in memory 22 using conventional fingerprint matching algorithms such as those offered in the commercially available GSRCH-G GRAMS/386 IR Search/Galactic for GRAMS/386 from Galactic Industries Corporation. The type of lubricant is identified automatically in accordance with the present invention based on the highest degree of correlation between the respective spectra.

Furthermore, it will be appreciated that the present invention has utility not simply for analyzing used lubricants. Rather, the present invention can be used in virtually any situation where it is desirable to automatically identify a type of lubricant. Moreover, the present invention has been described in the context of a primarily software based system. It will be appreciated, however, that the system can just as easily be implemented via a predominantly hardware based system.

The present invention includes all such equivalents and modifications, and is limited only by the scope of the following claims.

What is claimed is:

1. An apparatus for identifying a type of lubricant from among a plurality of different types of lubricants, comprising:

means for obtaining electromagnetic absorption data for a lubricant;

automated means for processing the electromagnetic absorption to determine at least one characteristic chemical property of the lubricant in the electromagnetic absorption spectrum data and for identifying a lubricant type based on the at least one characteristic chemical property; and means for outputting the lubricant type.

2. The apparatus of claim 1, wherein the means for obtaining comprises a spectrometer.

3. The apparatus of claim 2, wherein the spectrometer is an infrared spectrometer.

4. The apparatus of claim 1, wherein the automated means comprises a computer for receiving the electromagnetic absorption spectrum data from a spectrometer.

5. The apparatus of claim 1, wherein the means for processing analyzes the absorption spectrum data based on computer algorithms using fingerprint matching techniques to analyze correlation between the electromagnetic absorption spectrum data and other predetermined spectrum data.

6. The apparatus of claim 1, wherein the electromagnetic absorption spectrum data comprises data in the infrared spectrum.

7. The apparatus of claim 1, wherein the automated means further comprises means for further analyzing the electromagnetic absorption spectrum data as a function of the lubricant type to indicate and evaluate a use characteristic of the lubricant indicative of the condition of the lubricant.

8. The apparatus of claim 7, wherein the means for further analyzing processes the electromagnetic absorption spectrum data within a predefined range of spectral wavenumbers associated with the use characteristic.

9. An apparatus for identifying a type of lubricant, comprising:
   means for obtaining electromagnetic absorption spectrum data for a lubricant;
   automated means for processing the electromagnetic absorption spectrum data to determine at least one characteristic chemical property of the lubricant in the electromagnetic absorption spectrum data and for identifying a lubricant type based on the at least one characteristic chemical property;
   means for outputting the lubricant type; and
   wherein the lubricant type can include mineral lubricants and synthetic lubricants.

10. The apparatus of claim 1, wherein the output means comprises a display or printer.

11. An apparatus for automatically identifying and analyzing different types of used lubricants, comprising:
   means for obtaining electromagnetic absorption spectrum data for a lubricant;
   automated means for processing the electromagnetic absorption spectrum data to determine at least one characteristic chemical property of the lubricant, for identifying a lubricant type based on the at least one characteristic chemical property, and for analyzing the electromagnetic absorption spectrum data as a function of the lubricant type to indicate and evaluate a use characteristic of the lubricant indicative of the condition of the lubricant; and
   means for outputting information relating to the use characteristic of the lubricant.

12. The apparatus of claim 11, wherein the automated means comprises memory means for storing indicia of a plurality of different types of lubricants, and the automated means compares the electromagnetic absorption spectrum data to the indicia in order to determine the lubricant type.

13. The apparatus of claim 11, wherein the automated means automatically evaluates the use characteristic of the lubricant upon identifying the lubricant type.

14. The apparatus of claim 11, wherein the automated means functions to identify and analyze based on an analysis of predetermined wavenumber ranges included in the absorption spectrum data.

15. The apparatus of claim 11, wherein the use characteristic comprises at least one of Freon and sulfate content in the lubricant.

16. The apparatus of claim 11, wherein the electromagnetic absorption spectrum data comprises data in the infrared spectrum.

17. The apparatus of claim 11, whereby in order for the automated means to analyze the electromagnetic absorption spectrum data as a function of the lubricant type to indicate and evaluate a use characteristic, the automated means applies a different analysis criteria to different lubricant types.

18. An apparatus for automatically identifying and analyzing different types of used lubricants, comprising:
   means for obtaining electromagnetic absorption spectrum data for a lubricant;
   automated means for processing the electromagnetic absorption spectrum data to determine at least one characteristic chemical property of the lubricant, for identifying a lubricant type based on the at least one characteristic chemical property, and for analyzing the electromagnetic absorption spectrum data as a function of the lubricant type to indicate and evaluate a use characteristic of the lubricant indicative of the condition of the lubricant;
   means for outputting information relating to the use characteristic of the lubricant; and
   wherein said automated means causes an error message to be communicated by way of the output means in the event the automated means is unable to identify the lubricant type.

19. An apparatus for automatically identifying and analyzing different types of used lubricants, comprising:
   means for obtaining electromagnetic absorption spectrum data for a lubricant;
   automated means for processing the electromagnetic absorption spectrum data to determine at least one characteristic chemical property of the lubricant, for identifying a lubricant type based on the at least one characteristic chemical property, and for analyzing the electromagnetic absorption spectrum data as a function of the lubricant type to indicate and evaluate a use characteristic of the lubricant indicative of the condition of the lubricant;
   means for outputting information relating to the use characteristic of the lubricant; and
   wherein the lubricant type can include mineral lubricants and synthetic lubricants.

20. An apparatus for automatically identifying and analyzing different types of used lubricants, comprising:
   means for obtaining electromagnetic absorption spectrum data for a lubricant;
   automated means for processing the electromagnetic absorption spectrum data to determine at least one characteristic chemical property of the lubricant, for identifying a lubricant type based on the at least one characteristic chemical property, and for analyzing the electromagnetic absorption spectrum data as a function of the lubricant type to indicate and evaluate a use characteristic of the lubricant indicative of the condition of the lubricant;
   means for outputting information relating to the use characteristic of the lubricant; and
   wherein the lubricant type can include mineral lubricants, synthetic organic ester lubricants and phosphate ester lubricants.

21. An apparatus for automatically identifying and analyzing different types of used lubricants, comprising:
   means for obtaining electromagnetic absorption spectrum data for a lubricant;
   automated means for processing the electromagnetic absorption spectrum data to determine at least one characteristic chemical property of the lubricant, for identifying a lubricant type based on the at least one characteristic chemical property, and for analyzing the electromagnetic absorption spectrum data as a function of the lubricant type to indicate and evaluate a use characteristic of the lubricant indicative of the condition of the lubricant;
   means for outputting information relating to the use characteristic of the lubricant; and wherein the at least one characteristic chemical property is selected from a group of spectral data components including a $CH_2$-wagging component, a $CH_2$-scissoring component, a carbonyl component and a phosphate component.

22. An apparatus for identifying a type of lubricant, comprising:

means for obtaining electromagnetic absorption spectrum data for a lubricant;

automated means for processing the electromagnetic absorption spectrum data to determine at least one characteristic chemical property of the lubricant in the electromagnetic absorption spectrum data and for identifying a lubricant type based on the at least one characteristic chemical property;

means for outputting the lubricant type; and wherein the means for processing analyzes the electromagnetic absorption spectrum data to locate peaks in the electromagnetic absorption spectrum data, the peaks and their respective spectral wavenumbers representing the at least one characteristic chemical property.

23. The apparatus of claim 6, wherein the means for processing compares heights of the peaks in the electromagnetic absorption spectrum data with predefined amplitude values in order to identify the lubricant type.

24. The apparatus of claim 7, wherein the means for processing comprises a computer and memory, the predefined amplitude values being stored in the memory.

25. The apparatus of claim 6, wherein the means for processing "identifies peaks" in at least one of the wavenumber ranges selected from a group including approximately 1468 $cm^{-1}$ to 1448 $cm^{-1}$, 1380 $cm^{-1}$ to 1374 $cm^{-1}$, 1800 $cm^{-1}$ to 1700 $cm^{-1}$, and 1250 $cm^{-1}$ to 1120 $cm^{-1}$.

* * * * *